(12) United States Patent
Edelson (10) Patent No.: US 10,485,855 B2
(45) Date of Patent: Nov. 26, 2019

(54) DEMONSTRABLE EFFICACY ACROSS OR WITHIN PATIENT POPULATIONS

(71) Applicant: Anterios, Inc., New York, NY (US)

(72) Inventor: Jonathan Edelson, Scarsdale, NY (US)

(73) Assignee: Anterios, Inc., New York, NY (US)

( * ) Notice: Subject to any disclaimer, the term of this patent is extended or adjusted under 35 U.S.C. 154(b) by 0 days.

(21) Appl. No.: 14/702,269

(22) Filed: May 1, 2015

(65) Prior Publication Data

US 2015/0313536 A1    Nov. 5, 2015

Related U.S. Application Data

(60) Provisional application No. 61/987,089, filed on May 1, 2014.

(51) Int. Cl.
*A61B 5/00* (2006.01)
*A61K 38/48* (2006.01)
*A61K 9/00* (2006.01)
*G06Q 99/00* (2006.01)

(52) U.S. Cl.
CPC ........ *A61K 38/4893* (2013.01); *A61B 5/4266* (2013.01); *A61B 5/444* (2013.01); *A61B 5/4833* (2013.01); *A61B 5/4842* (2013.01); *A61B 5/4848* (2013.01); *A61K 9/0014* (2013.01); *G06Q 99/00* (2013.01); *A61B 5/441* (2013.01); *C12Y 304/24069* (2013.01)

(58) Field of Classification Search
CPC ....... A61B 5/4266; A61B 5/441; A61B 5/444; A61B 5/4833; A61B 5/4842; A61B 5/4848; A61K 38/4893; A61K 9/0014; C12Y 304/24069; G06Q 99/00
See application file for complete search history.

(56) References Cited

U.S. PATENT DOCUMENTS

| | | | |
|---|---|---|---|
| 2002/0086036 A1 | 7/2002 | Walker | |
| 2005/0074466 A1* | 4/2005 | Suskind | A61K 38/4893 424/247.1 |
| 2010/0049672 A1 | 2/2010 | Straube et al. | |
| 2010/0280975 A1 | 11/2010 | Wischik et al. | |
| 2011/0213219 A1 | 9/2011 | Bilello et al. | |
| 2012/0208858 A1* | 8/2012 | Shanler | A61K 9/0014 514/396 |
| 2012/0328549 A1* | 12/2012 | Edelson | A61K 31/20 424/66 |
| 2012/0328701 A1 | 12/2012 | Edelson et al. | |
| 2012/0328702 A1* | 12/2012 | Edelson | A61K 9/0014 424/490 |

OTHER PUBLICATIONS

Leyden et al. (2003) Journal of the American Academy of Dermatology 49(3): 5200-5210. (Year: 2003).*
International Search Report for International Patent Application No. PCT/US2015/028806, dated Jul. 20, 2015 (2 pages).
Supplementary European Search Report for Application No. 15785602.2, dated Nov. 7, 2017, 7 pages.

* cited by examiner

*Primary Examiner* — Lisa J Hobbs
(74) *Attorney, Agent, or Firm* — McCarter & English, LLP; Marcie B. Clarke; Mei Bai (57) ABSTRACT

The present invention provides methods for improving observed or determined efficacy by administration of agents to more severely diseased subjects, as contrasted with less severely diseased subjects. The present disclosure specifically demonstrates that, with respect to treatment of certain skin conditions, and particularly conditions associated with dysregulated and/or diseased skin cells, administration to more severely diseased subjects improves observed or determined efficacy.

8 Claims, 6 Drawing Sheets

Figure 6

DEMONSTRABLE EFFICACY ACROSS OR WITHIN PATIENT POPULATIONS

RELATED APPLICATIONS

This application claims priority to and benefit of U.S. Provisional application Ser. No. 61/987,089 filed May 1, 2014, the entire contents of which are incorporated herein by reference.

BACKGROUND

Current belief in the field of dermatology is that patients with skin conditions such as acne or hyperhidrosis respond to a given treatment at a given dose proportionately to the severity of their illness. For example, consider the study of patients who have acne, the most prevalent of all skin diseases: If hypothetical Patient A has 100 acne lesions on her face and hypothetical Patient B has 50 lesions on her face and they each receive a 50 mg pill of Agent X that has been shown to be an effective treatment for acne, then if Patient A has 50% reduction in the number of acne lesions (which in her case would be a reduction by 50 lesions) it would be expected that Patient B would have approximately a 50% reduction in acne lesions (which in her case would a reduction by 25 lesions). This assumption enables the comparison of patients within a study despite different patients being enrolled in the study with different levels of baseline disease severity. This assumption essentially "normalizes" changes in disease state due to treatment by reference to each patient's own baseline of disease. This assumption not only enables the comparison of patients within a study despite different patients being enrolled in the study with different levels of baseline disease severity, but it also enables the comparison of results across studies of similar (e.g., one retinoid cream versus another) or different treatments (e.g., a retinoid cream versus an antibiotic cream) for acne. The different treatments can be compared across studies by comparing the percent reductions in acne lesions for each treatment/study. See Webster (2011), who summarizes dozens of standard acne treatment clinical studies that use percent reductions in acne lesions as study outcome measures; Webster then compares these study results against one another using this same percent reduction in acne lesions for differing treatments.

Similarly, consider hyperhidrosis, a condition that is characterized by excessive sweating and affects about 3% of the population (or approximately 10 million people in the United States): If hypothetical Patient A has underarm sweating of 200 mg in 5 minutes and hypothetical Patient B produces 100 mg by comparison, and they each receive a 50 mg pill of Agent X that has been shown to be an effective treatment for hyperhidrosis, then if Patient A has 50% reduction in sweating (which in her case would be a reduction by 100 mg of sweat) it would be expected that Patient B would have approximately a 50% reduction in sweating (which in her case would a reduction by 50 mg of sweat). This assumption enables the comparison of patients within a study despite different patients being enrolled in the study with different levels of baseline disease severity. This assumption essentially "normalizes" changes in disease state due to treatment by reference to each patient's own baseline of disease. This assumption not only enables the comparison of patients within a study despite different patients being enrolled in the study with different levels of baseline disease severity, but it also enables the comparison of results across studies of similar (e.g., one pill versus another) or different treatments (e.g., a pill versus an injectable treatment) for hyperhidrosis. The different treatments can be compared across studies by comparing the percent reductions in sweat for each treatment/study. See, for example, Naumann (2001), Heckmann (2005), and Lowe (2007) which used the percent reduction in produced sweat as a standard parameter for each of these clinical trials.

SUMMARY

The present disclosure provides particular methods as described herein.

In certain embodiments, the present disclosure provides methods of improving demonstrable effectiveness of a treatment, the method comprising steps of determining stratification of subjects into two or more categories based on disease or condition severity, so that a first category corresponds to relatively severe disease or condition relative to at least one second category; and administering the treatment to subjects in the first category and not to subjects in at least one second category. In some embodiments, the relatively severe disease comprises elevated frequency or severity of disease symptoms, and/or earlier onset of such symptoms, relative to the at least one second category. In some embodiments, the disease or condition is a skin disease or condition. In some embodiments, the treatment comprises administration of botulinum toxin. In some embodiments, the disease or condition is selected from the group consisting of acne (in all its forms including acne vulgaris), excess sebum production, seborrhea, sebaceous hyperplasia, seborrhoeic dermatitis, sebaceous adenoma, sebaceous carcinoma, sebaceous cyst, oily skin, enlarged skin pores, psoriasis, hyperhidrosis, rosacea, atopic dermatitis, lupus, scleroderma, eczema, Raynaud's syndrome, herpes simplex, onychomycosis, warts, cellulitis, pruritus, vitiligo, melanoma, basal cell carcinoma, cutaneous lymphoma, hair loss, or wrinkles. In some embodiments, the disease or condition is selected from the group consisting of cancer, cardiovascular disease, diabetes, depression, anxiety, headache, migraine headache, glaucoma, heart burn, gastric ulcers, arthritis, overactive bladder, urinary incontinence, cervical dystonia, blepharospasm, strabismus, chronic pain, erectile dysfunction, and benign prostatic hyperplasia.

In certain embodiments, the present disclosure provides methods of administering treatment to subjects suffering from a disease or condition, the method comprising steps of determining severity of the disease or condition in individual subjects, so that each subject is determined to belong either to a first category or to one of at least one second category of severity; and administering a treatment to those subjects in the first category and not to subjects in at least one of the second category(ies). In some embodiments, the first category is of subjects suffering from relatively severe disease or condition. In some embodiments, the step of administering comprises administering a dosage of a pharmaceutical composition that would have an apparent lack of therapeutic benefit if administered to subjects in at least one of the second category(ies). In some embodiments, the step of administering comprises administering a pharmaceutical composition according to a dosing regimen that would have an apparent lack of therapeutic benefit if administered to subjects in at least one of the second category(ies). In some embodiments, the step of administering comprises topically administering the treatment. In some embodiments, the treatment comprises administration of botulinum toxin. In some embodiments, the disease or condition is selected from a group consisting of acne (in all its forms including acne vulgaris), excess sebum production, seborrhea, sebaceous hyperplasia, seborrhoeic dermatitis, sebaceous adenoma, sebaceous carcinoma, sebaceous cyst, oily skin, enlarged skin pores, psoriasis, hyperhidrosis, rosacea, atopic dermatitis, lupus, scleroderma, eczema, Raynaud's syndrome, herpes simplex, onychomycosis, warts, cellulitis, pruritus, vitiligo, melanoma, basal cell carcinoma, cutaneous lymphoma, hair loss, or wrinkles. In some embodiments, the disease or condition is selected from a group consisting of cancer, cardiovascular disease, diabetes, depression, anxiety, headache, migraine headache, glaucoma, heart burn, gastric ulcers, arthritis, overactive bladder, urinary incontinence, cervical dystonia, blepharospasm, strabismus, chronic pain, and benign prostatic hyperplasia.

In some embodiments, the present disclosure provides improvements to methods of treating subjects suffering from a disease or condition, for example by determining to which of two or more classifications of disease or condition severity a particular subject belongs; and administering to the particular subject a therapeutic regimen determined to be appropriate for the relevant classification, where different therapeutic regimens are indicated for different classifications. In some embodiments, the disease or condition is acne. In some embodiments, the disease or condition is hyperhidrosis. In some embodiments, the therapeutic regiment comprises botulinum toxin.

BRIEF DESCRIPTION OF THE DRAWING

FIG. 4 shows an exemplary graph that demonstrates the correlation between treatment effect (the difference between Active and Vehicle effects on Gravimetric Sweat Production) and Gravimetric Sweat Production at baseline prior to treatment.

FIG. 5 shows an exemplary graph that demonstrates the percent change in Gravimetric Sweat Production in subjects after treatment with Active or Vehicle and baseline Gravimetric Sweat Production ≥100 mg/5 minutes at baseline prior to treatment.

FIG. 6 shows an exemplary graph that demonstrates the percent change in Gravimetric Sweat Production in subjects after treatment with Active or Vehicle and baseline Gravimetric Sweat Production ≥200 mg/5 minutes at Baseline prior to treatment.

DEFINITIONS

Administration: As used herein, the term "administration" refers to the administration of a composition to a subject or system (e.g., to a cell, organ, tissue, organism, or relevant component or set of components thereof). Those of ordinary skill will appreciate that route of administration may vary depending, for example, on the subject or system to which the composition is being administered, the nature of the composition, the purpose of the administration, etc. In some embodiments, administration may involve intermittent dosing. In some embodiments, administration may involve continuous dosing (e.g., perfusion) for at least a selected period of time.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, refers to an observable biological effect or result achieved by an agent or entity of interest. For example, in some embodiments, a specific binding interaction is a biological activity. In some embodiments, modulation (e.g., induction, enhancement, or inhibition) of a biological pathway or event is a biological activity. In some embodiments, presence or extent of a biological activity is assessed through detection of a direct or indirect product produced by a biological pathway or event of interest.

Combination therapy: As used herein, the term "combination therapy" refers to those situations in which a subject is simultaneously exposed to two or more therapeutic regimens or modalities (e.g., to two or more therapeutic agents). In some embodiments, two or more regimens or modalities are administered or applied simultaneously (e.g., one or more individual doses of each of two or more agents, may be administered at substantially the same time); in some embodiments, such regimens or modalities may be administered sequentially (e.g., at least a first dose of a first agent is administered prior to at least a first dose of a second agent); in some embodiments, such regimens or modalities such that individual doses or applications overlap.

Comparable: As used herein, the term "comparable" describes two (or more) sets of conditions, circumstances, individuals, or populations that are sufficiently similar to one another to permit comparison of results obtained or phenomena observed. In some embodiments, comparable sets of conditions, circumstances, individuals, or populations are characterized by a plurality of substantially identical features and one or a small number of varied features. Those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied. Those skilled in the art will appreciate that relative language used herein (e.g., enhanced, activated, reduced, inhibited, etc) will typically refer to comparisons made under comparable conditions.)

Dosage form: (or "unit dosage form"), as used herein, refers to physically discrete unit of a therapeutic agent for a subject (e.g., a human patient) to be treated. In some embodiments, each unit contains a predetermined quantity of active material calculated or demonstrated to produce a desired therapeutic effect when administered to a relevant population according to an appropriate dosing regimen. For example, in some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). It will be understood, however, that the total dosage (e.g., total daily dosage) administered to any particular patient will typically be selected by a medical professional (e.g., a medical doctor) within the scope of sound medical judgment, and may include more than one such discrete unit, and/or may utilize a fraction of a discrete unit.

Dosing regimen: (or "therapeutic regimen"), as used herein is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, a therapeutic agent is administered once a day (QD) or twice a day (BID). In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Improve, increase, reduce, etc: As used herein, terms such as "improve", "increase", "reduce", etc., which necessarily imply a comparison, refer to a comparison with an appropriate comparable reference or standard. For example, in some embodiments, level and/or activity of an agent or marker of interest may be reduced under a set of conditions or circumstances of interest (e.g., after administration of therapy) as compared with its level and/or activity under a comparable set of conditions (e.g., prior to administration of the therapy or after administration of the therapy to an appropriate reference subject). In some embodiments, an appropriate reference may be a historical reference. In some embodiments, an appropriate reference may be an average, e.g., as may be observed within or across a relevant population.

Pharmaceutical composition: As used herein, the term "pharmaceutical composition" refers to a composition is used on or in the body to prevent, diagnose, alleviate, treat or cure a disease in humans or animals.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans). In some embodiments, a subject is a human.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, or condition (e.g., wounds, abnormal skin cell proliferation, tissue connective diseases such as scleroderma, pachyonychia congenita, skin inflammation, psoriasis, sunburn or other types of skin damage, skin cancer, etc.) has been diagnosed with or exhibits symptoms of the disease, disorder, or condition.

Symptoms are reduced: According to the present invention, "symptoms are reduced" when one or more symptoms of a particular disease, disorder or condition is reduced in magnitude (e.g., intensity, severity, etc.) or frequency. For purposes of clarity, a delay in the onset of a particular symptom is considered one form of reducing the frequency of that symptom. To give but a few examples, where the condition in question is acne, symptoms of that condition are reduced when the (e.g., diameter, volume, etc.) and/or severity (e.g., redness, inflammatory response, etc.) of one or more blemishes in the selected area is reduced, and/or when the number of total blemishes is reduced (e.g., on a subject's face, back, etc.). Where the condition in question is hyperhidrosis and/or unwanted sweating, symptoms are reduced when the subject produces less sweat. It is not intended that the present invention be limited only to cases where the symptoms are eliminated. The present invention specifically contemplates treatment such that one or more symptoms is/are reduced (and the condition of the subject is thereby "improved"), albeit not completely eliminated.

Therapeutically effective amount: As used herein, the term "therapeutically effective amount" means an amount that is sufficient, when administered to a population suffering from or susceptible to a disease, disorder and/or condition, to treat the disease, disorder and/or condition. In some embodiments, a therapeutically effective amount is one that reduces the incidence and/or severity of, and/or delays onset of, one or more symptoms of the disease, disorder and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. It is specifically understood that particular subjects may, in fact, be "refractory" to a "therapeutically effective amount." To give but one example, a refractory subject may have a low bioavailability such that clinical efficacy is not obtainable. In some embodiments, reference to a therapeutically effective amount may be a reference to an amount as measured in one or more specific tissues. Those of ordinary skill in the art will appreciate that, in some embodiments, a therapeutically effective agent may be formulated and/or administered in a single dose. In some embodiments, a therapeutically effective agent may be formulated and/or administered in a plurality of doses, for example, as part of a dosing regimen.

Therapeutic agent: As used herein, the phrase "therapeutic agent" refers to any agent that, when administered to a subject, has a therapeutic effect and/or elicits a desired biological and/or pharmacological effect.

Treatment: As used herein, the term "treatment" (also "treat" or "treating") refers to any administration of a substance (e.g., provided compositions) that partially or completely alleviates, ameliorates, relives, inhibits, delays onset of, reduces severity of, and/or reduces incidence of one or more symptoms or features of a particular disease, disorder and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder and/or condition.

Unwanted side effects: As used herein, the term "unwanted side effects" refers to one or more effects and/or symptoms associated with administration of a substance to a patient that are not the desired and/or intended effects and/or are unpleasant to the patient. Exemplary unwanted side effects include pain; bruising; ecchymosis; hematoma; botulism poisoning; unwanted systemic effects; undesirable blood levels of the administered substance; damage to underlying nervous tissue (e.g., neuronal paralysis); unwanted effects on muscles (e.g., muscle paralysis); flu-like symptoms; morbidity; mortality; alteration in body weight; alteration in enzyme levels; pathological changes detected at the microscopic, macroscopic, and/or physiological levels; infection; hemorrhage; inflammation; scarring; loss of function; changes in local blood flow; fever; malaise; teratogenesis; pulmonary hypertension; stroke; heart disease; heart attack; neuropathy; nausea; vomiting; dizziness; diarrhea; headache; dermatitis; dry mouth; addiction; miscarriage; abortion; uterine hemorrhage; birth defects; bleeding; cardiovascular disease; deafness; kidney damage and/or failure; liver damage and/or failure; dementia; depression; diabetes; erectile dysfunction; glaucoma; hair loss; anemia; insomnia; lactic acidosis; melasma; thrombosis; priapism; rhabdomyolysis; seizures; drowsiness; increase in appetite; decrease in appetite; increase in libido; decrease in libido; tardive dyskinesia; non-axillary sweating; injection site pain and hemorrhage; pharyngitis; neck pain; back pain; pruritus; anxiety; follicular obstruction; and/or combinations thereof. In some embodiments, topical administration of a provided composition reduces unwanted side effects by about 50%, about 60%, about 70%, about 80%, about 90%, about 95%, about 98%, about 99%, or about 100% relative to non-topical administration (e.g., injection, oral administration, etc.) of the same substance.

DESCRIPTION OF CERTAIN EMBODIMENTS

The present disclosure encompasses the surprising insight that, in some instances, efficacy of a particular pharmacologic treatment or therapeutic regimen as observed across a population of individuals suffering from a particular disease, disorder or condition, may vary in a manner correlated with severity of the disease, disorder or condition in the individuals. The present disclosure provides, among other things, technologies for stratifying patient populations (e.g., identifying individuals who are more or less likely to respond to the particular pharmacologic treatment or therapeutic regimen) and/or for improving therapy with the particular pharmacologic treatment or therapeutic regimen through administration preferentially or solely to individuals that are more likely to respond to the particular pharmacologic treatment or therapeutic regimen.

Diseases and Conditions

Teachings of the present disclosure are particularly exemplified in relation to certain skin conditions, and particularly conditions associated with disregulated and/or diseased skin cells. In some embodiments, the present invention provides methods for the treatment of a disease or condition selected from the group consisting of cancer, cardiovascular disease, diabetes, depression, anxiety, headache, migraine headache, glaucoma, heart burn, gastric ulcers, arthritis, overactive bladder, urinary incontinence, cervical dystonia, blepharospasm, strabismus, chronic pain, and benign prostatic hyperplasia.

Skin Conditions

The present invention provides methods for the treatment of any of a variety of skin diseases, disorders and/or conditions. In some embodiments, the present invention provides methods for the treatment of diseases, disorders, or conditions associated with activity of sweat and/or sebaceous glands. In some embodiments, the present invention provides methods and compositions for the treatment of diseases, disorders or conditions associated with the epidermal and/or dermal level of the skin.

In some embodiments, the present invention provides methods for the treatment of one or more of acne (in all its forms including acne vulgaris), excess sebum production, seborrhea, sebaceous hyperplasia, seborrhoeic dermatitis, sebaceous adenoma, sebaceous carcinoma, sebaceous cyst, oily skin, enlarged skin pores, psoriasis, hyperhidrosis, rosacea, atopic dermatitis, lupus, scleroderma, eczema, Raynaud's syndrome, herpes simplex, onychomycosis, warts, cellulitis, pruritus, vitiligo, melanoma, basal cell carcinoma, cutaneous lymphoma, hair loss, wrinkles and/or combinations thereof.

Acne

In some embodiments, the present invention provides methods for the treatment of acne vulgaris (commonly referred to as "acne"), a skin disease caused by changes in the pilosebaceous units (i e, skin structures comprising a hair follicle and its associated sebaceous gland). In some embodiments, acne is inflammatory. In some embodiments, acne is noninflammatory. While not life-threatening, acne vulgaris can cause significant problems for affected individuals. Depending on its severity and other factors, recalcitrant acne can be psychologically debilitating, and can impose significant financial and emotional costs on those whom it afflicts. Despite some recent successes in acne therapy, treatment failures are still common, especially in adult women. While many adults "outgrow" this disease, there are some who continue to be afflicted during much of adulthood, despite continued medical advances. There is an unfilled need for a more effective treatment for acne, particularly severe acne, and one with minimal side effects.

In general, acne develops as a result of blockages in follicles. The pathology centers on the pilosebaceous units, comprising a sebaceous gland, a follicle (i.e., pore), and a vellus hair. Among the first events leading to acne are hyperkeratinization and formation of a plug of keratin and sebum (a "microcomedo"), obstructing the upper region of a follicle. Enlargement of sebaceous glands and an increase in sebum production occur with increased androgen production at adrenarche. A microcomedo may enlarge to form an open comedo (a "blackhead") or closed comedo (a "whitehead"). In these conditions the naturally occurring largely commensal bacteria *Propionibacterium acnes* can cause inflammation, leading to inflammatory lesions (papules, infected pustules, or nodules) in the dermis around the microcomedo or comedo, which results in redness and may result in scarring or hyperpigmentation.

Adolescence is marked by an increase in levels of circulating androgens, particularly dehydroepiandrosterone sulfate (DHEAS). Increased androgen levels are thought to cause sebaceous glands to enlarge and to increase sebum production. While most acne patients have normal hormone levels, there are reasons to conclude that increased sebum production plays a role in acne. For example, there may be a correlation between the rate of sebum production and the severity of acne. In addition, acne patients typically produce sebum that is deficient in linoleic acid, which is a potential cause of abnormal keratinization and follicular obstruction.

In response to increased sebum levels, *Propionibacterium acnes*, a relatively slow growing, typically aerotolerant anaerobic gram positive, diphtheroid bacterium, often colonizes the sebaceous follicles. *P. acnes* exacerbates acne by acting as a chemo-attractant for neutrophils. Neutrophils ingest *P. acnes*, and in doing so release various hydrolytic enzymes that damage the follicular wall. Released follicular contents then invade the dermis and cause an inflammatory reaction, manifesting as pustules, erythematous papules, or nodules. In a separate route, *P. acnes* can hydrolyze triglycerides to free fatty acids, which also increase inflammation and follicular obstruction. *P. acnes* may also activate the complement components of the immune system, which can also lead to follicular obstruction.

Follicles are lined with squamous epithelium, a layer of cells that is contiguous with the skin surface. In an acne-prone individual, the shedding of cells from this lining is often impeded, perhaps due to an increased level of intercellular adhesion that promotes the retention of cells. Retained cells can obstruct follicles, resulting in comedones. Such inhibited shedding may be related to abnormalities in epidermal differentiation and/or to abnormal sebum composition (e.g., a deficiency in linoleic acid). It has also been demonstrated that increased sebum levels can irritate keratinocytes, causing the release of interleukin-1, which in turn can cause follicular hyperkeratinization. In general, each of these acne-causing routes, which are not mutually exclusive, is associated with follicular obstruction.

Several factors are known to be linked to acne, including, but not limited to, family and/or genetic history (see, e.g., Ballanger et al., 2006, Dermatology, 212: 145-149; incorporated herein by reference); hormonal activity (e.g., menstrual cycles, puberty, etc.); stress (e.g., through increased output of hormones from the adrenal glands); hyperactive sebaceous glands; accumulation of dead skin cells; bacteria in the pores (e.g., *P. acnes*); skin irritation or scratching; use of anabolic steroids; use of medications containing halogens (e.g., iodides, chlorides, bromides), lithium, barbiturates, or androgens; exposure to certain chemical compounds (e.g., dioxins such as chlorinated dioxins); exposure to testosterone, dihydrotestosterone (DHT), dehydroepiandrosterone sulfate (DHEAS), and/or insulin-like growth factor 1 (IGF-I); diet including milk and/or high levels of carbohydrate; low levels of vitamins A and/or E; poor hygiene; or any combinations thereof.

In some embodiments, acne treatments work via one or more of the following mechanisms: (1) normalizing shedding into the pore to prevent blockage; (2) killing *P. acnes*; (3) having antiinflammatory activity; and/or (4) manipulating hormone levels.

The present invention provides methods of treating acne comprising determining severity of the acne in individual subjects, so that each subject is determined to belong either to a first category or to one of at least one second category of severity; and administering a treatment to those subjects in the first category and not to subjects in at least one of the second category(ies).

Hyperhidrosis

Hyperhidrosis is a medical condition in which a person sweats excessively and unpredictably. People with hyperhidrosis can sweat even when the temperature is cool, and when they are at rest. Sweating helps the body stay cool and is perfectly natural. People sweat more in warm temperatures, when they exercise, or in response to situations that make them nervous, angry, embarrassed, or afraid. Uncontrollable sweating can lead to significant discomfort, both physical and emotional.

Hyperhidrosis occurs without normal sweat triggers, and refers to the condition characterized by perspiration in excess of that required for regulation of body temperature. Those with hyperhidrosis appear to have overactive sweat glands. Hyperhidrosis can either be generalized or localized to specific parts of the body. Hands, feet, axillae, forehead, and the groin area are among the most active regions of perspiration due to the relatively high concentration of sweat glands; however, any part of the body may be affected. Excessive sweating that affects hands, feet, and armpits and has no other identifiable cause is referred to as "primary" or "focal hyperhidrosis." Primary hyperhidrosis affects 2%-3% of the population, yet less than 40% of patients with this condition seek medical advice. There may be a genetic component involved in primary hyperhidrosis. One theory is that hyperhidrosis results from an overactive sympathetic nervous system. Primary hyperhidrosis is found to start during adolescence or even before.

If sweating occurs as a result of another medical condition, it is called secondary hyperhidrosis. Sweating may be all over one's body, or it may be localized to one area. Secondary hyperhidrosis can start at any point in life. For some, it can seem to come on unexpectedly. Conditions that cause secondary hyperhidrosis include but are not limited to, acromegaly, hyperthyroidism, glucose control disorders (including diabetes), pheochromocytoma, carcinoid syndrome, cancer, tuberculosis, infections, menopause, spinal cord injury, stroke, thyroid gland disorder, pituitary gland disorder, gout, mercury poisoning, Parkinson's disease, heart disease, lung disease, certain medications, substance abuse, or anxiety conditions.

Hyperhidrosis can be categorized as "palmar" (i.e., excessive sweating of the hands), "axillary" (i.e., excessive sweating of the armpits), "plantar" (i.e., excessive sweating of the feet), "facial" (i.e., excessive sweating of the face), "cranial" (i.e., excessive sweating of the head, especially noted around the hairline), or "general" (i.e., overall excessive sweating).

The present invention provides methods of treating hyperhidrosis comprising determining severity of the hyperhidrosis in individual subjects, so that each subject is determined to belong either to a first category or to one of at least one second category of severity; and administering a treatment to those subjects in the first category and not to subjects in at least one of the second category(ies).

Stratification of Subjects

The present invention provides technologies for improving demonstrable effectiveness of a treatment, comprising steps of determining stratification of subjects into two or more categories. In some embodiments, stratification is based on disease or condition severity. In some embodiments, stratification of subjects into two or more categories comprises stratification into a first category that corresponds to relatively severe disease or condition relative to at least one second category. In some embodiments, treatment is administered to subjects in the first category and not to subjects in at least one second category. In some embodiments, the relatively severe disease comprises elevated frequency or severity of disease symptoms, and/or earlier onset of such symptoms, relative to the at least one second category. In some embodiments, the disease or condition is a skin disease or condition. In some embodiments, treatment comprises administration of botulinum toxin.

In some embodiments, teachings of the present disclosure relate to a disease or condition selected from the group consisting of acne (in all its forms including acne vulgaris), excess sebum production, seborrhea, sebaceous hyperplasia, seborrhoeic dermatitis, sebaceous adenoma, sebaceous carcinoma, sebaceous cyst, oily skin, enlarged skin pores, psoriasis, hyperhidrosis, rosacea, atopic dermatitis, lupus, scleroderma, eczema, Raynaud's syndrome, herpes simplex, onychomycosis, warts, cellulitis, pruritus, vitiligo, melanoma, basal cell carcinoma, cutaneous lymphoma, hair loss, or wrinkles.

In some embodiments teachings of the present disclosure relate to a disease or condition selected from the group consisting of cancer, cardiovascular disease, diabetes, depression, anxiety, headache, migraine headache, glaucoma, heart burn, gastric ulcers, arthritis, overactive bladder, urinary incontinence, cervical dystonia, blepharospasm, strabismus, chronic pain, and benign prostatic hyperplasia.

Determining Severity of Disease or Condition

The present invention includes, among other things, determining severity of a disease or condition in individual subjects. In some embodiments, a disease or condition comprises symptoms manifested as specific biochemical, anatomical or physiological changes. In some embodiments, determining severity of a disease or condition comprises comparing one or more symptoms exhibited by a subject to a symptom or set of symptoms (e.g., to a spectrum of symptoms) displayed (e.g., typically displayed) by subjects that manifest the biochemical, anatomical or physiological changes that characterize a disease or condition. In some embodiments, determining severity of a disease or condition comprises comparing the symptoms exhibited by a subject to symptoms accepted by the medical field to be characteristic of a disease or condition. In some embodiments, relative severity of a disease or disorder comprises elevated frequency of disease symptoms. In some embodiments, relative severity of a disease or disorder comprises earlier onset of disease symptoms.

In some embodiments, subjects are stratified into two categories based on disease or condition severity, so that the first category corresponds to relatively severe disease or condition relative to the second category. In some embodiments, subjects are stratified into two or more categories based on disease or condition severity, so that a first category corresponds to relatively severe disease or condition relative to at least one second category.

In some embodiments, a relevant disease or condition (e.g., for which severity is to be determined) is selected from the group consisting of cancer, cardiovascular disease, diabetes, depression, anxiety, headache, migraine headache, glaucoma, heart burn, gastric ulcers, arthritis, overactive bladder, urinary incontinence, cervical dystonia, blepharospasm, strabismus, chronic pain, and benign prostatic hyperplasia. In some embodiments, the disease or condition (e.g., for which severity is to be determined) is selected from the group consisting of acne (in all its forms including acne vulgaris), excess sebum production, seborrhea, sebaceous hyperplasia, seborrhoeic dermatitis, sebaceous adenoma, sebaceous carcinoma, sebaceous cyst, oily skin, enlarged skin pores, psoriasis, hyperhidrosis, rosacea, atopic dermatitis, lupus, scleroderma, eczema, Raynaud's syndrome, herpes simplex, onychomycosis, warts, cellulitis, pruritus, vitiligo, melanoma, basal cell carcinoma, cutaneous lymphoma, hair loss, wrinkles and/or combinations thereof. One of ordinary skill in the art will appreciate the biochemical, anatomical or physiological changes that characterize a disease or condition and the methods and criteria for determining disease severity.

Acne

Acne is diagnosed by the identification of lesions. The spectrum of acne lesions ranges from noninflammatory open or closed comedones (blackheads and whiteheads) to inflammatory lesions, which may be papules, pustules, or nodules. Lesions are most likely to occur on the face, neck, chest, and back, where there is a higher concentration of sebaceous glands. Other conditions can mimic acne, and even include the term acne in their nomenclature, but they lack the presence of comedones. In some embodiments, grading acne based on the type of lesions and their severity can help in deciding which therapies are warranted.

Hyperhidrosis

Practical, qualitative, and quantitative methods are available for the diagnosis of hyperhidrosis. During the evaluation of a patient with primary hyperhidrosis, it is sometimes necessary to assess the rate of sweat production, the specific areas involved, the effect of the condition on the patient's quality of life, and the impairment of daily activities. Such approaches can also be used, for example in accordance with the present invention, when selecting and/or stratifying patients for clinical trials (e.g., for potential treatments of hyperhidrosis) and/or for administration of a particular therapy.

Many experts believe that it is important to observe the patient sweating during an office visit. For axillary involvement, an assessment of the sweat stains of shirts and blouses can be useful. In some cases, a sweat stain with a diameter less than 5 cm is normal. Mild hyperhidrosis can be associated with stains 5 to 10 cm in diameter and still confined to the armpit. Stains of 10 to 20 cm are seen in moderate hyperhidrosis, while stains over 20 cm reaching the waistline are common in severe hyperhidrosis. For palmar hyperhidrosis, a low grade of involvement would be a moist palmar surface without visible droplets of perspiration. If palmar sweating extends toward the fingertips, the condition can be considered moderate, and if sweat drips off the palm and reaches all the fingertips, it is severe.

A quantitative approach to assessing severity is gravimetric measurement, which can be done on the palm and in the axilla. It is important to note that gravimetric measurement is often utilized in clinical trials and is not part of routine clinical practice. After drying the surface, a preweighed filter paper is applied to the palm or axilla for a period of time measured by stopwatch. The paper can then be weighed and the rate of sweat production can be calculated in mg/min.

Disease severity may alternatively or additionally be assessed by scales and questionnaires administered to patients, for example the Hyperhidrosis Disease Severity Scale, that assesses how tolerable a patient's sweating is to the patient. Other scales and questionnaires address the impact of excessive sweating on the quality of the patient's life and/or the degree of embarrassment the sweating causes the patient. Such scales and questionnaires may also be used to make or confirm a diagnosis.

Treatment

The present invention provides technologies for administering treatment to subjects suffering from a disease or condition, which may, in some embodiments, comprise steps of determining severity of the disease or condition in individual subjects, so that each subject is determined to belong either to a first category or to one of at least one second category of severity; and administering a treatment to those subjects in the first category and not to subjects in at least one of the second category(ies). In some embodiments, treatment is administered to those subjects stratified in a first category as having been determined to have a relatively severe disease or condition relative to at least one second category.

In some embodiments, the present invention involves administration of at least one treatment to subjects in the first category according to a dosing regimen sufficient to achieve a reduction in the degree and/or prevalence of a relevant condition of at least about 20%; in some embodiments according to a dosing regimen sufficient to achieve a of at least about 25%; in some embodiments according to a dosing regimen sufficient to achieve a reduction of at least about 30%; in some embodiments according to a dosing regimen sufficient to achieve a reduction of at least about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, or more.

In some embodiments, the present invention involves administration of at least one treatment to subjects in the first category according to a dosing regimen sufficient to achieve a reduction in the degree and/or prevalence of a relevant condition of at least about 20% in a specified percentage of a population of patients to which the composition was administered; in some embodiments according to a dosing regimen sufficient to achieve a of at least about 25% in a specified percentage of a population of patients to which the composition was administered; in some embodiments according to a dosing regimen sufficient to achieve a reduction of at least about 30% in a specified percentage of a population of patients to which the composition was administered; in some embodiments according to a dosing regimen sufficient to achieve a reduction of at least about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90% or more in a specified percentage of a population of patients to which the composition was administered. In some embodiments, the specified percentage of population of patients to which the composition was administered is at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. To give but a few illustrative examples, in some embodiments, the present invention involves administration of at least one provided composition according to a dosing regimen sufficient to achieve a reduction in the degree and/or prevalence of a relevant dermatologic condition of at least about 20% in at least about 50% of the population of patients to which the composition was administered. In some embodiments, the present invention involves administration of at least one provided composition according to a dosing regimen sufficient to achieve a reduction in the degree and/or prevalence of a relevant dermatologic condition of at least about 30% in at least about 50% of the population of patients to which the composition was administered.

In some embodiments, the present invention involves administration of at least one treatment to subjects in the first category, wherein the treatment is formulated for any route of administration described herein. In some embodiments the treatment is formulated for topical administration. In some embodiments, the treatment is formulated into a cream, liniment, lotion, gel, shampoo, conditioner, sunscreen, deodorant, and/or antiperspirant (e.g., as a roll-on, solid stick, gel, cream, aerosol, etc.), as appropriate to the condition being treated.

In some embodiments, the treatment is formulated for injection, e.g., into an affected site. In some embodiments, provided compositions are formulated for systemic delivery.

In some embodiments the treatment is administered locally to an affected site (e.g., axillae, hands, feet, scalp, hair follicle, face, neck, back, arms, chest, etc., as appropriate to the particular condition being treated). In some embodiments, local administration is achieved by topical administration and/or by injection. In some embodiments, a provided composition is administered systemically (e.g., orally, topically, via injection, etc.).

In some embodiments, the treatment may be a therapeutic agent or biological material, such as cells, proteins, peptides, nucleic acid analogues, nucleotides, oligonucleotides, nucleic acids (DNA, RNA, siRNA), peptide nucleic acids, aptamers, antibodies or fragments or portions thereof, antigens or epitopes, hormones, hormone antagonists, growth factors or recombinant growth factors and fragments and variants thereof, cell attachment mediators (such as RGD), cytokines, enzymes, anti-inflammation agent, antifungals, antivirals, toxins, prodrugs, chemotherapeutic agents, small molecules, drugs (e.g., drugs, amino acids, vitamins, antioxidants), other antimicrobial compounds, and combinations thereof.

In some embodiments, the treatment may be neurotransmitters, hormones, intracellular signal transduction agents, pharmaceutically active agents, toxic agents, chemical toxins, biological toxins, microbes, and animal cells. The active agents may also include therapeutic compounds, such as pharmacological materials, vitamins, sedatives, hypnotics, prostaglandins and radiopharmaceuticals.

Botulinum Toxin

In some embodiments, the treatment administered to those subjects stratified in a first category as having been determined to have a relatively severe disease or condition relative to at least one second category is botulinum toxin. Botulinum toxin (BTX) is produced in nature by the anaerobic, gram positive bacillus *Clostridium botulinum* and is a potent polypeptide neurotoxin. Most notably, BTX causes a neuroparalytic illness in humans and animals referred to as botulism. BTX can apparently pass through the lining of the gut and attack peripheral motor neurons. Symptoms of botulinum toxin intoxication can progress from difficulty walking, swallowing, and speaking to paralysis of the respiratory muscles, and death.

The different serotypes of botulinum toxin vary in the animal species that they affect and in the severity and duration of the paralysis they evoke. For example, it has been determined that BTX-A is 500 times more potent than is BTX-B, as measured by the rate of paralysis produced in the rat. Additionally, BTX-B has been determined to be non-toxic in primates at a dose of 480 U/kg, which is about 12 times the primate LD50 for BTX-A. Furthermore, it is known that botulinum toxin type B has, upon intramuscular injection, a shorter duration of activity and is also less potent than BTX-A at the same dose level.

Botulinum toxin apparently binds with high affinity to cholinergic motor neurons, is translocated into the neuron and blocks the release of acetylcholine and other pre-formed mediators and transmitters. For example, in vitro studies performed on neurons other than motor neurons revealed that botulinum toxin not only blocks acetylcholine release, but can also prevent liberation of other neurotransmitters (e.g., neurotransmitters stored in vesicles), including small organic molecules and neuropeptides (e.g., adrenaline; noradrenaline; dopamine; glutamate; aspartate; glycine; GABA; ATP that is co-stored with neurotransmitters such as acetylcholine and/or glutamate; substance P; and/or CGRP) (Poulain, 2008, Botulinum J., 1:14; incorporated herein by reference).

Botulinum toxins have been used in clinical settings for the treatment of certain neuromuscular disorders. In particular, BTX-A has been approved by the U.S. Food and Drug Administration for the treatment of cervical dystonia in adults to decrease the severity of abnormal head position and neck pain associated with cervical dystonia; the treatment of severe primary axillary hyperhidrosis that is inadequately managed with topical agents; the treatment of strabismus and blepharospasm associated with dystonia, including benign essential blepharospasm or VII nerve disorders in patients 12 years of age and above; and for the temporary improvement in the appearance of moderate to severe glabellar lines associated with corrugator and/or procerus muscle activity in adult patients ≤65 years of age.

Clinical effects of peripheral intramuscular BTX-A are usually seen within one week of injection. The typical duration of symptomatic relief from a single intramuscular injection of BTX-A averages about three months.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kilodalton (kD) synaptosomal associated protein (SNAP-25), but they target different amino acid sequences within this protein. Botulinum toxin types B, D, F and G act on vesicle-associated membrane protein (VAMP, also called synaptobrevin), with each serotype cleaving the protein at a different site. Finally, botulinum toxin type C1 has been shown to cleave both syntaxin and SNAP-25. These differences in mechanism of action may affect the relative potency and/or duration of action of the various botulinum toxin serotypes. The cytosol of pancreatic islet B cells contains at least SNAP-25 (Gonelle-Gispert et al., 1999, Biochem. J., 339 (pt 1): 159-65; incorporated herein by reference), and synaptobrevin.

As noted above, botulinum toxin for use in accordance with the present invention can be derived from any source. For purposes of completeness, however, we note that a variety of sources, including commercial sources, for certain botulinum toxin preparations are readily available. In some embodiments, botulinum toxin is selected from the group consisting of type A, type Ab, type Af, type B, type Bf, type C1, type C2, type D, type E, type F, and type G; mutants thereof; variants thereof; fragments thereof; characteristic portions thereof; and/or fusions thereof. In some embodiments, botulinum toxin is present as any of the subtypes described in Sakaguchi, 1982, Pharmacol. Ther., 19:165; and/or Smith et al., 2005, Infect. Immun., 73:5450; both of which are incorporated herein by reference.

Administration/Formulations

As described herein, the present invention provides methods of administering treatment to a subject for various applications including, for example, cosmetic and/or medical applications. In some embodiments, the present invention provides methods of treating diseases, disorders, and/or conditions associated with activity of epidermal and/or dermal structures (e.g., sweat glands, sebaceous glands, hair follicles, etc.) by administering provided compositions to a subject in need thereof.

In some embodiments, the present invention provides methods of administration of provided compositions via any route of delivery, including, but not limited to, oral (PO), intravenous (IV), intramuscular (IM), intra-arterial, intramedullary, intrathecal, subcutaneous (SQ), intraventricular, transdermal, interdermal, rectal (PR), vaginal, intraperitoneal (IP), intragastric (IG), topical and/or transdermal (e.g., by lotions, creams, liniments, ointments, powders, gels, drops, wipes, pads, etc.), mucosal; and/or combinations thereof.

In some embodiments, provided methods involve topical, transdermal, or intradermal administration of provided compositions to the skin of a subject. In some embodiments, such routes achieve local delivery.

In light of the present disclosure, those skilled in the art would readily be able to identify appropriate groups suffering from "severe" forms of a given disease, disorder, or condition. In some embodiments, subjects suffering from "severe" disease are members of a group that display elevated frequency or severity of disease symptoms, and/or show earlier onset of such symptoms, as compared with a different group of diseases sufferers.

REFERENCES

Webster GF. Evidence-based review: fixed-combination therapy and topical retinoids in the treatment of acne. J Drugs Dermatol 2011; 10(6):636-644.

Naumann et al. Botulinum Toxin Type A in treatment of bilateral primary axillary hyperhidrosis: randomized, parallel group, double-blind, placebo controlled trial BMJ 2001; 323:596-600.

Heckmann et al. Low dose efficacy of Botulinum Type A for axillary hyperhidrosis. Arch Dermatol 2005; 141:1255-1259.

Lowe et al. Botulinum Type A in the treatment of axillary hyperhidrosis. J Am Acad Dermatol 2007; 56:604-611.

Ballanger et al. Heredity: a prognostic factor for acne. Dermatology 2006; 212: 145-149.

Poulain et al. How do the Botulinum Neurotoxins block neurotransmitter release: from botulism to the molecular mechanism of action. Botulinum J. 2008; 1:14.

Gonelle-Gispert et al. SNAP-25a and -25b isoforms are both expressed in insulin-secreting cells and can function in insulin secretion. Biochem. J. 1999; 339 (pt 1): 159-65.

Sakaguchi G. *Clostridium botulinum* toxins. Pharmacol. Ther. 1982; 19:165.

Smith et al. Sequence Variation within Botulinum Neurotoxin Serotypes Impacts Antibody Binding and Neutralization. Infect. Immun. 2005; 73:5450.

EXEMPLIFICATION

Example 1: Effect of Topical Botulinum on Acne

Figure 1:
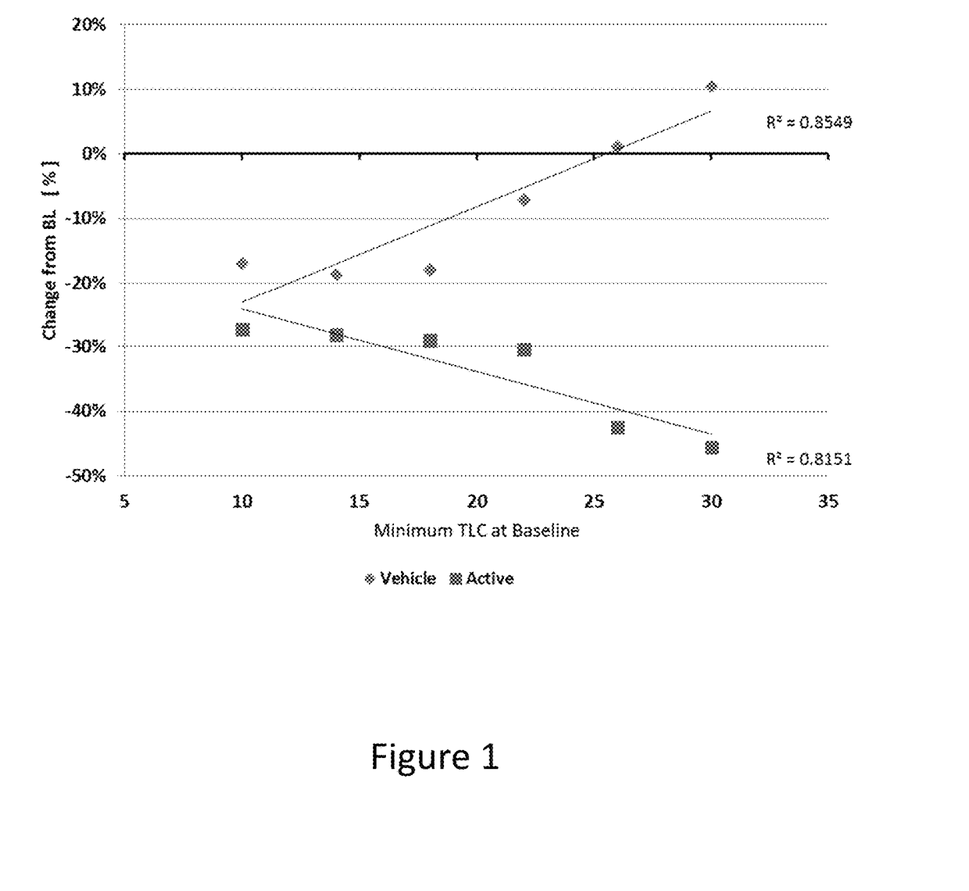
FIG. 1 shows an exemplary graph that demonstrates the correlation between percent change in Total Lesion Count after treatment and Total Lesion Count at baseline prior to treatment when people were treated with either a topical botulinum treatment (Active) or vehicle.
Figure 2:
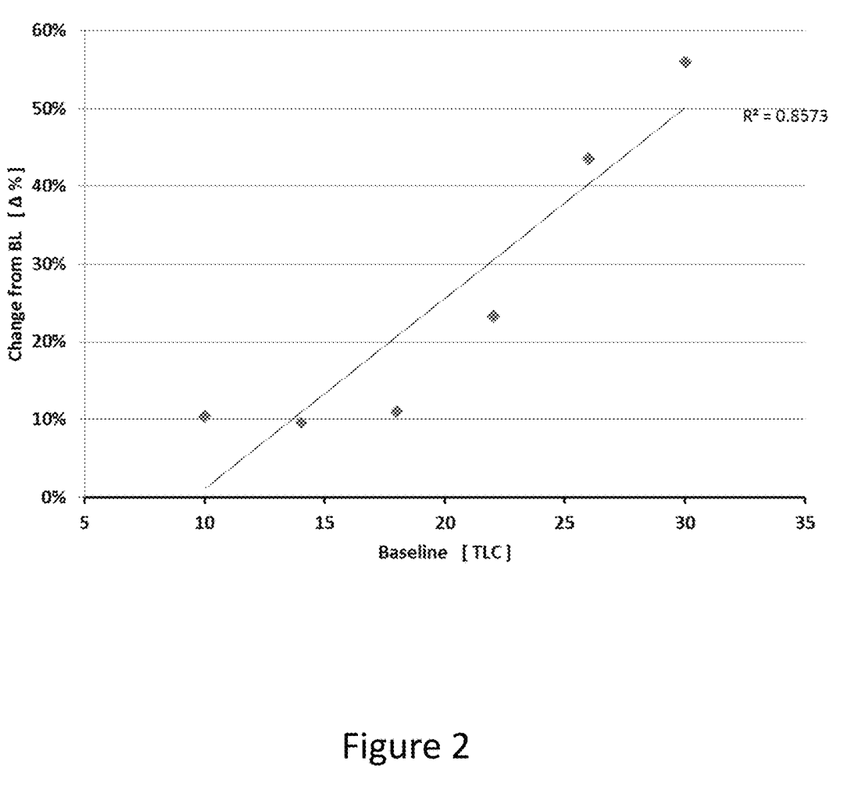
FIG. 2 shows an exemplary graph that demonstrates the correlation between treatment effect (the difference between Active and Vehicle effects on Total Lesion Count) and Total Lesion Count at baseline prior to treatment.
Figure 3:
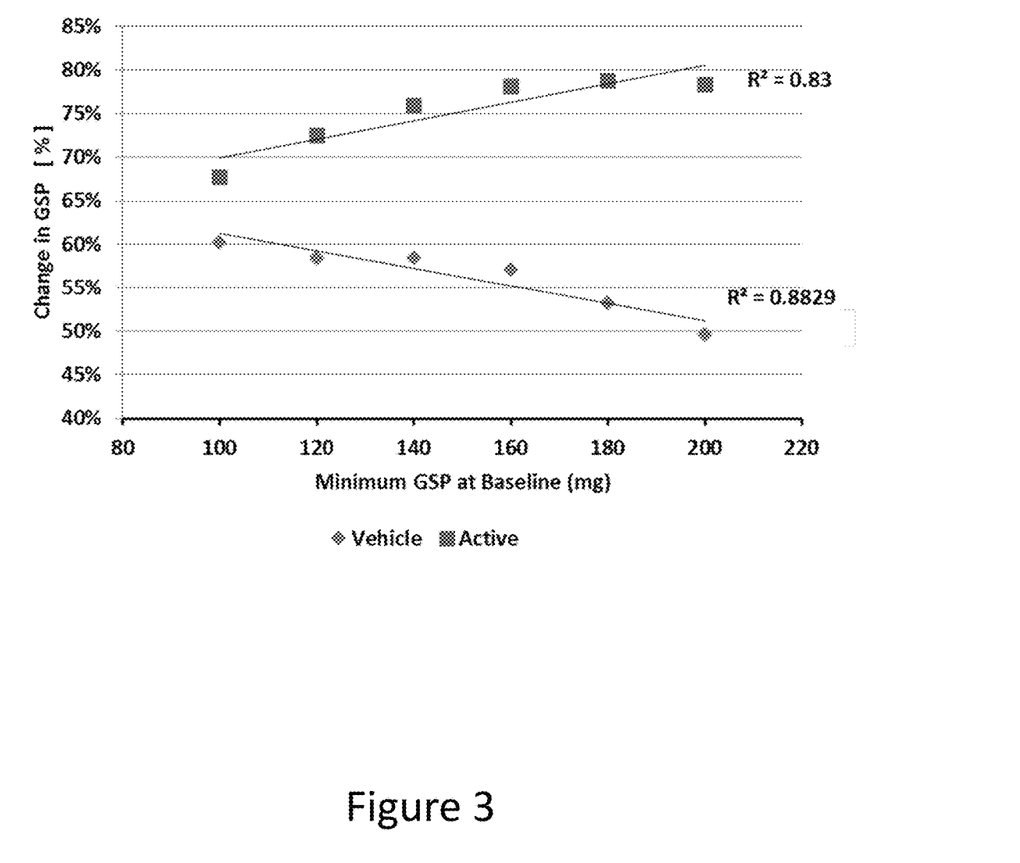
FIG. 3 shows an exemplary graph that demonstrates the correlation between percent change in Gravimetric Sweat Production after treatment with either a topical botulinum treatment (Active) or vehicle and Gravimetric Sweat Production at baseline prior to treatment.

A clinical study was conducted to assess the therapeutic effects of topical botulinum on acne. Acne lesion counts were made by the investigator at baseline prior to treatment and then after treatment. As shown in FIGS. 1-2, the greater the baseline disease severity that a patient had, the disproportionately greater response to treatment that a patient had, although all patients received the same dose of drug. The implications of these unexpected and surprising findings are that patients having more diseased states (e.g., severe) would respond to a much greater extent than subjects who have less diseased states (e.g., mild). Since disease covers a spectrum, the far end of one spectrum is no disease, going to mild, then moderate, and finally severe disease. Without wishing to be bound by any particular theory, the present inventors propose that this surprising finding might by attributable, at least in part to dysregulation of severely diseased skin (e.g., acne) caused by mechanism "Y" (hyper-sebum production), which might render such skin hypersensitive to a given dose through action at this dysregulated mechanism, while subjects with must less disease severity may not respond well (or may respond with minor improvements) compared to controls. For example, see FIG. 2, which compares the therapeutic response of a treatment when all subjects are included, many of which are not severely diseased (i.e., inclusion in the group if they have 10 or more acne lesions) which was observed to be a 10 percentage point treatment effect to the therapeutic response of those with severe disease (i.e., inclusion in the group if they have 30 or more acne lesions) which was observed to be a 55 percentage point treatment effect. What is observed in the first group that includes the less severe disease is a modest difference between the active treatment containing the drug and the vehicle, which does not contain the drug. What is observed in the second group that includes only the severely diseased is a dramatic difference between active treatment and vehicle. If the first group is considered only, this is a drug that may not be approved for commercial sale by regulatory authorities because of an apparent lack of therapeutic benefit when considered on clinical or statistical grounds. By comparison, if the second group of the severely diseased is considered, this is a drug would likely be approved by regulatory authorities because of the demonstration of a substantial therapeutic benefit when considered on clinical or statistical grounds. Understanding this dynamic, a drug manufacturer may choose to study only the more severe patients with the disease in order to increase the probability of a drug approval by the regulatory agencies. Likewise, a regulatory agency may only approve a drug for such patients. And, finally, a physician may only choose to treat patients with the more severe form of the disease because those are the patients who would benefit and demonstrate the most favorable balance between treatment reward and treatment risk of side-effects.

Example 2: Effect of Botulinum Toxin on Hyperhidrosis

Figure 4:
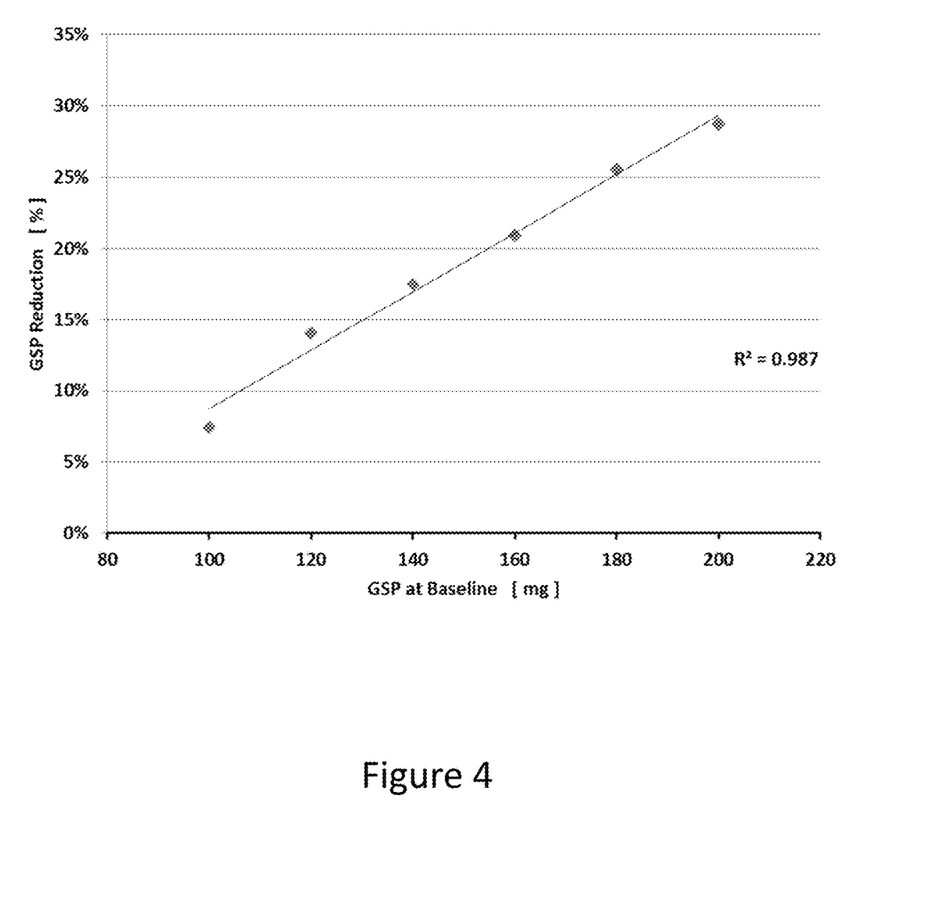
Figure 5:
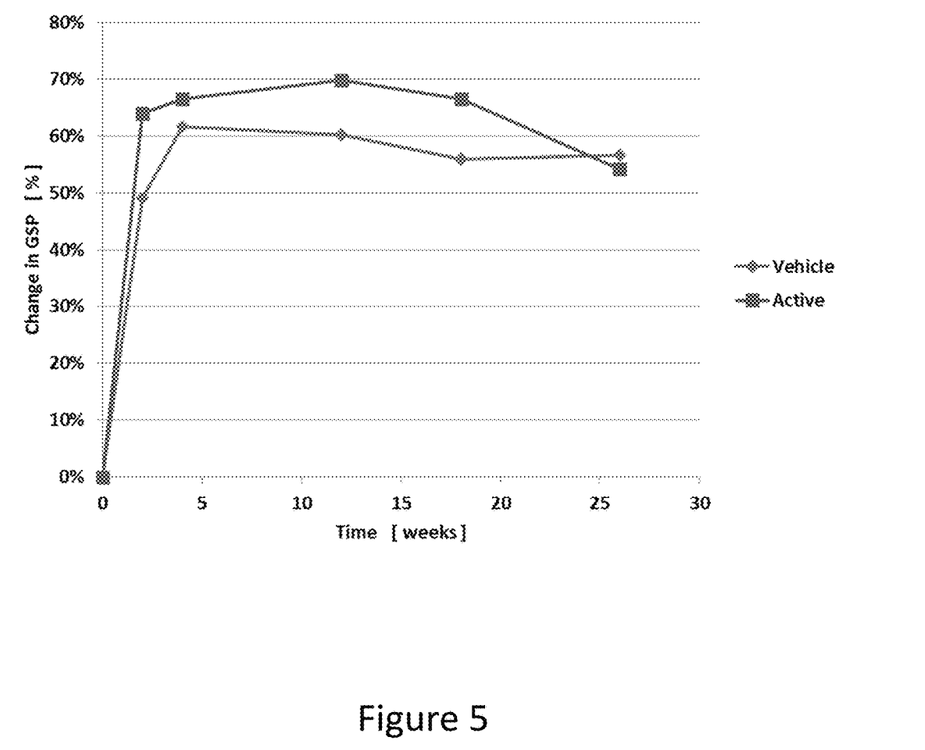
Figure 6:
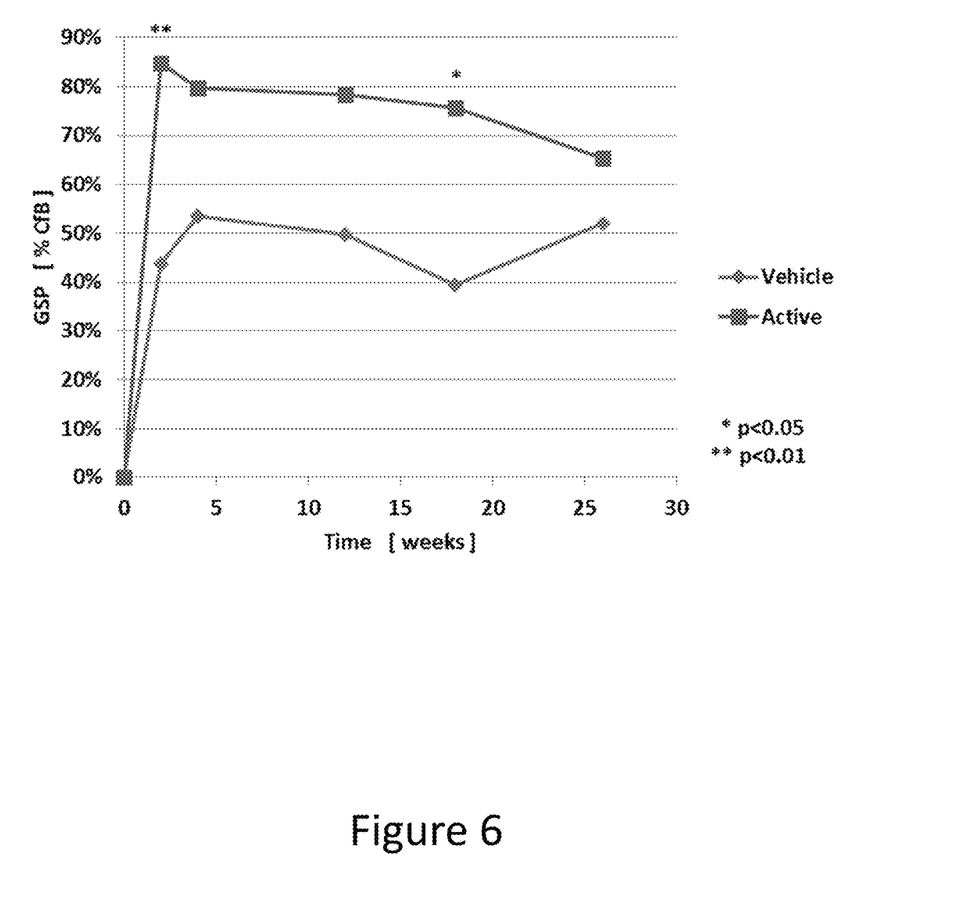

A clinical trial was conducted to assess the therapeutic effects of topical botulinum on hyperhidrosis (excessive sweating). Sweat production levels called "gravimetric sweat production" or "GSP" were made by the investigator at baseline prior to treatment and then after treatment. As demonstrated in FIGS. 3-6, the greater the baseline disease severity that a patient had, the disproportionately greater response to treatment that a patient had, although all patients received the same dose of drug. In fact, the percent reduction in gravimetric sweat production was highly correlated to baseline disease severity as noted in the FIG. 4. The implications of these unexpected and surprising findings are that patients having more diseased states (e.g., severe) would respond to a much greater extent than subjects who have less diseased states (e.g., mild). Since disease covers a spectrum, the far end of one spectrum is no disease, going to mild, then moderate, and finally severe disease. Without wishing to be bound by any particular theory, the present inventors propose that this surprising finding might by attributable, at least in part to dysregulation of severely diseased skin (e.g., hyperhidrosis) caused by mechanism "Z" (hyper-sweat production),), which might render such skin hypersensitive to a given dose through action at this dysregulated mechanism, while subjects with must less disease severity may not respond well (or may respond with minor improvements) compared to control. For example, see FIGS. 5-6, which compares the therapeutic response of a treatment when all subjects are included, many of which are not severely diseased (i.e., inclusion in the group if they have 100 mg GSP) to the therapeutic response of those with severe disease (i.e., inclusion in the group if they have 200 mg GSP or more). What is observed in the first group that includes the less severe disease is a modest difference between the active treatment containing the drug and the vehicle, which does not contain the drug. What is observed in the second group that includes only the severely diseased is a dramatic difference between active treatment and vehicle. If the first group is considered only, this is a drug that may not be approved for commercial sale by regulatory authorities because of an apparent lack of therapeutic benefit when considered on clinical or statistical grounds. By comparison, if the second group of the severely diseased is considered, this is a drug would likely be approved by regulatory authorities because of the demonstration of a substantial therapeutic benefit when considered on clinical or statistical grounds. Understanding this dynamic, a drug manufacturer may choose to study only the more severe patients with the disease in order to increase the probability of a drug approval by the regulatory agencies. Likewise, a regulatory agency may only approve a drug for such patients. And, finally, a physician may only choose to treat patients with the more severe form of the disease because those are the patients who would benefit and demonstrate the most favorable balance between treatment reward and treatment risk of side-effects.

EQUIVALENTS AND SCOPE

The foregoing has been a description of certain non-limiting preferred embodiments of the invention. Those skilled in the art will recognize, or be able to ascertain using no more than routine experimentation, many equivalents to the specific embodiments of the invention described herein. Those of ordinary skill in the art will appreciate that various changes and modifications to this description may be made without departing from the spirit or scope of the present invention, as defined in the following claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise. In addition, the invention encompasses compositions made according to any of the methods for preparing compositions disclosed herein.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Any embodiment, element, feature, application, or aspect of the compositions and/or methods of the invention can be excluded from any one or more claims. For purposes of brevity, all of the embodiments in which one or more elements, features, purposes, or aspects is excluded are not set forth explicitly herein.

I claim:

1. A method comprising steps of:
   a) determining the severity of acne in individual subjects by stratifying the subjects into two or more categories based on acne severity, so that a first category comprises subjects having severe acne relative to a second category that comprises subjects having acne who are not severely diseased; wherein the subjects having severe acne have 30 or more acne lesions; and wherein the subjects having acne who are not severely diseased have fewer than 20 acne lesions; and
   b) administering a treatment to subjects in the first category and not to subjects not in the first category, wherein the treatment comprises transdermal administration of botulinum toxin A;
   wherein the treatment has been demonstrated to achieve a decrease of 45% or more in the total number of acne lesions when administered to subjects in the first category; and not to achieve said decrease when administered to subjects in the second category.

2. The method of claim 1, wherein the acne in the subjects having severe acne is characterized by elevated frequency or severity of disease symptoms, and/or earlier onset of such symptoms, relative to the acne in the subjects having acne who are not severely diseased.

3. The method of claim 1, wherein the transdermal administration comprises topical administration.

4. A method comprising steps of:

administering a treatment to subjects suffering from severe acne, and not to subjects suffering from acne that is not severe, wherein severe acne is defined as having 20 or more acne lesions and acne that is not severe is defined as having fewer than 20 acne lesions, wherein the treatment comprises transdermal administration of botulinum toxin A in a vehicle;

and further wherein the treatment has been demonstrated to achieve a more dramatic difference relative to a vehicle control in severe acne than in acne that is not severe, wherein the more dramatic difference comprises a decrease of 20% or more in number of acne lesions.

5. The method of claim 4, wherein severe acne is defined as having 25 or more acne lesions and acne that is not severe is defined as having fewer than 25 acne lesions, and wherein the more dramatic difference comprises a decrease of 35% or more in the total number of acne lesions.

6. The method of claim 4, wherein severe acne is defined as having 30 or more acne lesions and acne that is not severe is defined as having fewer than 30 acne lesions, and wherein the more dramatic difference comprises a decrease of 50% or more in the total number of acne lesions.

7. The method of claim 4, wherein the acne in the subjects having severe acne is characterized by elevated frequency or severity of disease symptoms, and/or earlier onset of such symptoms, relative to the acne in the subjects having acne that is not severe.

8. The method of claim 4, wherein the transdermal administration comprises topical administration.

* * * * *